(12) United States Patent
Zablocki et al.

(10) Patent No.: US 6,214,807 B1
(45) Date of Patent: Apr. 10, 2001

(54) C-PYRAZOLE $_{2AA}$ RECEPTOR AGONISTS

(75) Inventors: Jeff A. Zablocki; Venkata P. Palle, both of Mountain View; Elfatih O. Elzein, Freemont, all of CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 09/338,327

(22) Filed: Jun. 22, 1999

(51) Int. Cl.$^7$ .......................... A61K 31/70; A01N 43/04
(52) U.S. Cl. .................. 514/46; 514/45; 514/47; 536/27.3; 536/27.6; 536/27.61; 536/27.7
(58) Field of Search .................. 514/45, 46, 47; 536/27.3, 27.61, 27.6, 27.7

(56) References Cited

U.S. PATENT DOCUMENTS

| | | |
|---|---|---|
| 4,956,345 | 9/1990 | Miyasaka et al. . |
| 5,189,027 | 2/1993 | Miyashita et al. . |
| 5,270,304 | 12/1993 | Kogi et al. . |
| 5,459,254 | 10/1995 | Yamaguchi et al. . |
| 5,593,975 | 1/1997 | Cristalli . |
| 5,705,491 | 1/1998 | Yamada . |
| 5,770,716 | 6/1998 | Khan et al. . |
| 5,939,543 | 8/1999 | Morozumi et al. . |

FOREIGN PATENT DOCUMENTS

| | | |
|---|---|---|
| 965411 | 4/1975 | (CA) . |
| 5-9197 | 1/1993 | (JP) . |

OTHER PUBLICATIONS

Marumoto, et al., "Synthesis and Coronary Vadodilating Activity of 2–Subsituted Adenosines", *Chem., Pharm. Bull.* 23(4): 759–774 (1975).

Marumoto, et al., "Synthesis and Enzymatic Activity of Adenosine 3',5'–Cyclic Phosphate Analogs", *Chem., Pharm. Bull.* 27(4) 990–1003 (1979).

Persson, et al., "Synthesis and Antiviral Effects of 2–Heteroaryl Substituted Adenosine and 8–Heteroaryl Substituted Guanosine Derivatives", *Bioorganic & Medicinal Chemistry,* 3: 1377–1382 (1995).

Mager, et al., "Molecular simulation applied to 2–(N'alkylidenehydrazino)– and 2–(N'–aralkylidenehydrazino) adenosine $A_2$ Agnonists", *Eur J. Med. Chem,* 30:15–25 (1995).

Cristalli et al., "2–Alkynl Derivatives of Adenosine 5'–N'ethyluronamide: Selective $A_2$ Adenosine Receptor Agonists with Potent Inhibitory Activity on Platelet Aggregation", *J. Med. Chem,* 37:1720–1726 (1994).

Matsuda, et al., "Nucleosides and Nucleotides. 103. 2–Alkynyladenoines: A Novel Class of Selective Adenosine $A_2$ Receptor Agonists with Potent Antihypertensive Effects", *J. Med. Chem.* 35:241–252 (1992).

*Primary Examiner*—James O. Wilson
(74) *Attorney, Agent, or Firm*—McDonnell, Boehnen, Hulbert & Berghoff

(57) ABSTRACT

2-adenosine C-pyrazole compositions having the following formula:

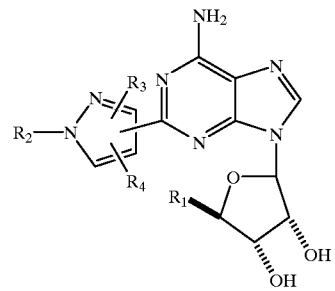

and methods for using the compositions as A2A receptor agonists to stimulate mammalian coronary vasodilatation for therapeutic purposes and for purposes of imaging the heart.

33 Claims, No Drawings

C-PYRAZOLE $_{2AA}$ RECEPTOR AGONISTS

BACKGROUND OF THE INVENTION

1. Field of Invention

This invention includes C-pyrazole compositions that are useful as $A_{2A}$ receptor agonists. The compositions of this invention are vasodialating agents that are useful in heart imaging to aid in the identification of mammals, and especially humans who are suffering from disorders such poor coronary perfusion which is indicative of coronary artery disease (CAD). The compositions of this invention can also be used as therapeutics for coronary artery disease.

2. Description of the Art

Pharmacological stress is frequently induced with adenosine or dipyridamole in patients with suspected CAD before imaging with Tl scintigraphy or echocardiography. Both drugs effect dilation of the coronary resistance vessels by activation of cell surface $A_2$ receptors. Although pharmacological stress was originally introduced as a mean of provoking coronary dilation in patients unable to exercise, several studies have shown that the prognostic value of $^{201}$Tl or echocardiographic imaging in patients subjected to pharmacological stress with adenosine or dipyridamole was equivalent to patients subjected to traditional exercise stress tests. However, there is a high incidence of drug-related adverse side effects during pharmacological stress imaging with these drugs such as headache and nausea, that could be improved with new therapeutic agents.

Adenosine $A_{2B}$ and $A_3$ receptors are involved in a mast cell degranulation and, therefore, asthmatics are not give the non-specific adenosine agonists to induce a pharmacological stress test. Additionally, adenosine stimulation of the $A_1$ receptor in the atrium and A-V mode will diminish the S-H interval which can induce AV block. (N. C. Gupto et al.; *J. Am Coll. Cardiol;* (1992) 19: 248–257). Also, stimulation of the adenosine A1 receptor by adenosine maybe responsible for the nausea since the $A_1$ receptor is found in the intestinal tract. (J. Nicholls et al.; *Eur. J. Pharm.* (1997) 338(2) 143–150).

Animal data suggests that specific adenosine $A_{2A}$ subtype receptors on coronary resistance vessels mediate the coronary dilatory responses to adenosine, whereas subtype $A_{2B}$ receptor stimulation relaxes peripheral vessels (note: the latter lowers systemic blood pressure). As a result there is a need for pharmaceutical compositions that are $A_2A$ receptor agonists that have no pharmacological effect as a result of stimulating the $A_1$ receptor in vivo. Furthermore, there is a need for $A_{2A}$ receptor agonists that have a short half-life, and that are well tolerated by patients undergoing pharmacological coronary stress evaluations.

SUMMARY OF THE INVENTION

In one aspect, this invention includes 2-adenosine C-pyrazole compositions that are useful A2A receptor agonists.

In another aspect, this invention includes pharmaceutical compositions including 2-adenosine C-pyrazole that are well tolerated with few side effects.

Still another aspect of this invention are C-pyrazole compositions that can be easily used in conjunction with radioactive imaging agents to facilitate coronary imaging.

In one embodiment, this invention includes C-pyrazole compositions having the following formula:

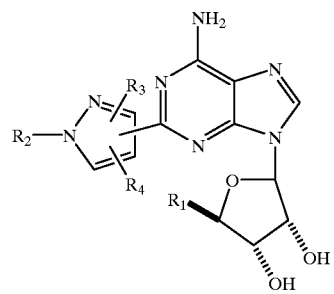

In another embodiment, this invention includes methods for using compositions of this invention to stimulate coronary vasodilatation in mammals, and especially in humans, for stressing the heart to induce a steal situation for purposes of imaging the heart.

In still another embodiment, this invention is a pharmaceutical composition of matter comprising one or more compositions of this invention and one or more pharmaceutical excipients.

DESCRIPTION OF THE CURRENT EMBODIMENTS

This compositions of this invention include a class of 2-adenosine C-pyrazole compounds having the following formula:

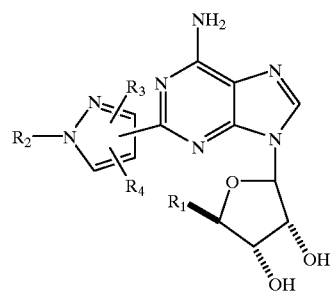

wherein $R^1$ is —CH$_2$OH, and —C(=O)NR$^5$R$^6$;

$R^2$ is selected from the group consisting of hydrogen, C$_{1-15}$ alkyl, C$_{2-15}$ alkenyl, C$_{2-15}$ alkynyl, heterocyclyl, aryl, and heteroaryl, wherein the alkyl, alkenyl, alkynyl, aryl, heterocyclyl, and heteroaryl substituents are optionally substituted with from 1 to 3 substituents independently selected from the group consisting of halo, NO$_2$, heterocyclyl, aryl, heteroaryl, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CO$_2$R$^{22}$, SO$_2$NR$^{20}$CON(R$^{20}$)$_2$, N(R$^{20}$)$_2$ NR$^{20}$COR$^{22}$, NR$^{20}$CO$_2$R$^{22}$, NR$^{20}$CON(R$^{20}$)$_2$, NR$^{20}$C(NR$^{20}$)NHR$^{23}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$ and wherein each optional heteroaryl, aryl, and heterocyclyl substituent is optionally substituted with halo, NO$_2$, alkyl, CF$_3$, amino, mono- or di- alkylamino, alkyl or aryl or heteroaryl amide, NCOR$^{22}$, NR$^{20}$SO$_2$R$^{22}$, COR$^{20}$, CO$_2$R$^{20}$, CON(R$^{20}$)$_2$, NR$^{20}$CON(R$^{20}$)$_2$, OC(O)R$^{20}$, OC(O)N(R$^{20}$)$_2$, SR$^{20}$, S(O) R$^{22}$, SO$_2$R$^{22}$, SO$_2$N(R$^{20}$)$_2$, CN, or OR$^{20}$;

$R^3$, $R^4$ are individually selected from the group consisting of hydrogen, C$_{1-15}$ alkyl, C$_{2-15}$ alkenyl, C$_{2-15}$ alkynyl, heterocyclyl, aryl, and heteroaryl, halo, NO$_2$, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CO$_2$R$^{22}$, SO$_2$NR$^{20}$CON(R$^{20}$)$_2$, N(R$^{20}$)$_2$ NR$^{20}$COR$^{22}$, NR$^{20}$CO$_2$R$^{22}$, NR$^{20}$CON(R$^{20}$)$_2$, NR$^{20}$C(NR$^{20}$)NHR$^{23}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$ wherein the alkyl, alkenyl, alkynyl, aryl, heterocyclyl, and heteroaryl substituents are optionally substituted with from 1 to 3 substituents individually selected from the group consisting of halo, NO$_2$, heterocyclyl, aryl, heteroaryl, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CO$_2$R$^{22}$, SO$_2$NR$^{20}$CON(R$^{20}$)$_2$, N(R$^{20}$)$_2$ NR$^{20}$COR$^{22}$, NR$^{20}$CO$_2$R$^{22}$, NR$^{20}$CON(R$^{20}$)$_2$, NR$^{20}$C(NR$^{20}$)NHR$^{23}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$ and wherein each optional heteroaryl, aryl, and heterocyclyl substituent is optionally substituted with halo, NO$_2$, alkyl, CF$_3$, amino, mono- or di- alkylamino, alkyl or aryl or heteroaryl amide, NCOR$^{22}$, NR$^{20}$SO$_2$R$^{22}$, COR$^{20}$, CO$_2$R$^{20}$, CON(R$^{20}$)$_2$, NR$^{20}$CON(R$^{20}$)$_2$, OC(O)R$^{20}$, OC(O)N(R$^{20}$)$_2$, SR$^{20}$, S(O)R$^{22}$, SO$_2$R$^{22}$, SO$_2$N(R$^{20}$)$_2$, CN, or OR$^{20}$;

R$^5$ and R$^6$ are each individually H, C$_{1-15}$ alkyl with from 1 to 2 substituents independently selected from the group consisting of halo, NO$_2$, heterocyclyl, aryl, heteroaryl, CF$_3$, CN, OR$^{20}$, SR$^{20}$, N(R$^{20}$)$_2$, S(O)R$^{22}$, SO$_2$R$^{22}$, SO$_2$N(R$^{20}$)$_2$, SO$_2$NR$^{20}$COR$^{22}$, SO$_2$NR$^{20}$CO$_2$R$^{22}$, SO$_2$NR$^{20}$CON(R$^{20}$)$_2$, N(R$^{20}$)$_2$ NR$^{20}$COR$^{22}$, NR$^{20}$CO$_2$R$^{22}$, NR$^{20}$CON($^{20}$)$_2$, NR$^{20}$C(NR$^{20}$)NHR$^{23}$, COR$^{20}$, CO$_2$R$^{20}$, CON(R$^{20}$)$_2$, CONR$^{20}$SO$_2$R$^{22}$, NR$^{20}$SO$_2$R$^{22}$, SO$_2$NR$^{20}$CO$_2$R$^{22}$, OCONR$^{20}$SO$_2$R$^{22}$, OC(O)R$^{20}$, C(O)OCH$_2$OC(O)R$^{20}$, and OCON(R$^{20}$)$_2$ and wherein each optional heteroaryl, aryl, and heterocyclyl substituent is optionally substituted with halo, NO$_2$, alkyl, CF$_3$, amino, mono- or di- alkylamino, alkyl or aryl or heteroaryl amide, NCOR$^{22}$, NR$^{20}$SO$_2$R$^{22}$, COR$^{20}$, CO$_2$R$^{20}$, CON(R$^{20}$)$_2$, NR$^{20}$CON(R$^{20}$)$_2$, OC(O)R$^{20}$, OC(O)N(R$^{20}$)$_2$, SR$^{20}$, S(O)R$^{22}$, SO$_2$R$^{22}$, SO$_2$N($^{20}$)$_2$, CN, or OR$^{20}$, R$^{20}$ is selected from the group consisting of H, C$_{1-15}$ alkyl, C$_{2-15}$ alkenyl, C$_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—C$_{1-6}$ alkyl, CF$_3$, aryl, and heteroaryl; and R$^{22}$ is a member selected from the group consisting of C$_{1-15}$ alkyl, C$_{2-15}$ alkenyl, C$_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—C$_{1-6}$ alkyl, CF$_3$, and heteroaryl wherein, when R$^1$=CH$_2$OH,R$^3$ is H, R$^4$ is H, the pyrazole ring is attached through C$^4$, and R$^2$ is not H.

When the compound is selected has one of the following formulas:

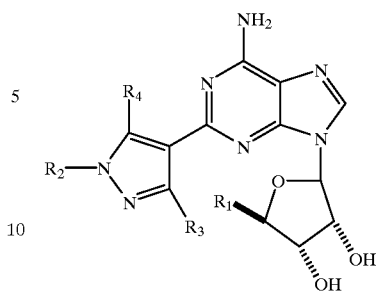

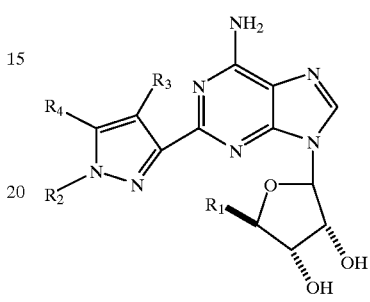

then it is preferred that R$^1$ is —CH$_2$OH; R$^2$ is selected from the group consisting of hydrogen, C$_{1-8}$ alkyl wherein the alkyl is optionally substituted with one substituent independently selected from the group consisting of aryl, CF$_3$, CN, and wherein each optional aryl substituent is optionally substituted with halo, alkyl, CF$_3$ or CN; and R$^3$ and R$^4$ are each independently selected from the group consisting of hydrogen, methyl and more preferably, R$^3$ and R$^4$ are each hydrogen.

When the composition of this invention has the following formula:

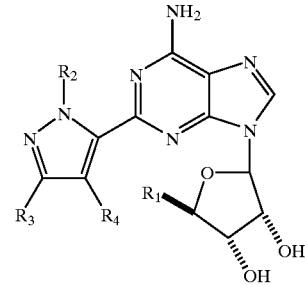

then it is preferred that R$^1$ is —CH$_2$OH; R$^2$ is selected from the group consisting of hydrogen, and C$_{1-6}$ alkyl, and more preferably selected from hydrogen and methyl; R$^3$ is selected from the group consisting of hydrogen, C$_{1-6}$ alkyl, aryl, wherein the alkyl, and aryl substituents are optionally substituted with from 1 to 2 substituents independently selected from the group consisting of halo, aryl, CF$_3$, CN, and wherein each optional aryl substituent is optionally substituted with halo, alkyl, CF$_3$ or CN; and R$^4$ is selected from the group consisting of hydrogen and C$_{1-6}$ alkyl, and more preferably, R$^4$ is selected from hydrogen and methyl.

It is most preferred that the compositions of this invention is selected from (4S,2R,3R,5R)-2-{6-amino-2-[1-benzylpyrazol-4-yl]purin-9-yl}-5-(hydroxymethyl)oxolane-3,4-diol, (4S,2R,3R,5R)-2-[6-amino-2-(1-pentylpyrazol-4-yl)purin-9yl]-5-(hydroxymethyl)oxolane-3,4-diol, (4S,2R,3R,5R)-2-[6-amino-2-(1-methylpyrazol-4-yl)purin-9-yl]-5-hydroxymethyl)oxolane-3,4-diol, (4S,2R,3R,5R)-2-{6- amino-2-[1-(methylethyl)pyrazol-4-yl]purin-9-yl}-5-(hydroxymethyl)oxolane-3,4-diol, (4S,2R,3R,5R)-2-{6-amino-2-[1-(3-phenylpropyl)pyrazol-4-yl]purin-9-yl}-5-(hydroxymethyl)oxolane-3,4-diol, (4S,2R,3R,5R)-2-{6-amino-2-[1-(4-t-butylbenzyl)pyrazol-4-yl]purin-9-yl}-5-(hydroxymethyl)oxolane-3,4-diol, (4S,2R,3R,5R)-2-(6-amino-2-pyrazol-4-ylpurin-9-yl)-5-(hydroxymethyl)oxolane-3,4-diol, and mixtures thereof.

The following definitions apply to terms as used herein.

"Halo" or "Halogen"—alone or in combination means all halogens, that is, chloro (Cl), fluoro (F), bromo (Br), iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl, branched alkyl or cycloalkyl. Preferably, straight or branched alkyl groups containing from 1–15, more preferably 1 to 8, even more preferably 1–6, yet more preferably 1–4 and most preferably 1–2, carbon atoms, such as methyl, ethyl, propyl, isopropyl, butyl, t-butyl and the like. The term "lower alkyl" is used herein to describe the straight chain alkyl groups described immediately above. Preferably, cycloalkyl groups are monocyclic, bicyclic or tricyclic ring systems of 3–8, more preferably 3–6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. A substituted alkyl is a straight chain alkyl, branched alkyl, or cycloalkyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Alkenyl"—alone or in combination means a straight, branched, or cyclic hydrocarbon containing 2–20, preferably 2–17, more preferably 2–10, even more preferably 2–8, most preferably 24 carbon atoms and at least one, preferably 1–3, more preferably 1–2, most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. A substituted alkenyl is the straight chain alkenyl, branched alkenyl or cycloalkenyl group defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxy, alkoxycarbonyl, aryloxycarbonyl, heteroaryloxycarbonyl, or the like attached at any available point to produce a stable compound.

"Alkynyl"—alone or in combination means a straight or branched hydrocarbon containing 2–20, preferably 2–17, more preferably 2–10, even more preferably 2–8, most preferably 2–4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di- substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like attached at any available point to produce a stable compound.

"Alkyl alkenyl" refers to a group —R—CR'=CR'" R"", where R is lower alkyl, or substituted lower alkyl, R', R'", R"" may independently be hydrogen, halogen, lower alkyl, substituted lower alkyl, acyl, aryl, substituted aryl, hetaryl, or substituted hetaryl as defined below.

"Alkyl alkynyl" refers to a groups —RC≡CR' where R is lower alkyl or substituted lower alkyl, R' is hydrogen, lower alkyl, substituted lower alkyl, acyl, aryl, substituted aryl, hetaryl, or substituted hetaryl as defined below.

"Alkoxy" denotes the group —OR, where R is lower alkyl, substituted lower alkyl, acyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

"Alkylthio" denotes the group —SR, —S(O)$_{n=1-2}$—R, where R is lower alkyl, substituted lower alkyl, aryl, substituted aryl, aralkyl or substituted aralkyl as defined herein.

"Acyl" denotes groups —C(O)R, where R is hydrogen, lower alkyl substituted lower alkyl, aryl, substituted aryl and the like as defined herein.

"Aryloxy" denotes groups —OAr, where Ar is an aryl, substituted aryl, heteroaryl, or substituted heteroaryl group as defined herein.

"Amino" denotes the group NRR', where R and R' may independently by hydrogen, lower alkyl, substituted lower alkyl, aryl, substituted aryl, hetaryl, or substituted hetaryl as defined herein or acyl.

"Amido" denotes the group —C(O)NRR', where R and R' may independently by hydrogen, lower alkyl, substituted lower alkyl, aryl, substituted aryl, hetaryl, substituted hetaryl as defined herein.

"Carboxyl" denotes the group —C(O)OR, where R is hydrogen, lower alkyl, substituted lower alkyl, aryl, substituted aryl, hetaryl, and substituted hetaryl as defined herein.

"Aryl"—alone or in combination means phenyl or naphthyl optionally carbocyclic fused with a cycloalkyl of preferably 5–7, more preferably 5–6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl"—alone or in combination means a monocyclic aromatic ring structure containing 5 or 6 ring atoms, or a bicyclic aromatic group having 8 to 10 atoms, containing one or more, preferably 14, more preferably 1–3, even more preferably 1–2, heteroatoms independently selected from the group O, S, and N, and optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl oxathiadiazolyl, isothiazolyl, tetrazolyl, imidazolyl, triazinyl, furanyl, benzofuryl, indolyl and the like. A substituted heteroaryl contains a substituent attached at an available carbon or nitrogen to produce a stable compound.

"Heterocyclyl"—alone or in combination means a non-aromatic cycloalkyl group having from 5 to 10 atoms in which from 1 to 3 carbon atoms in the ring are replaced by heteroatoms of O, S or N, and are optionally benzo fused or fused heteroaryl of 5–6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like. A substituted hetercyclyl contains a substituent nitrogen attached at an available carbon or nitrogen to produce a stable compound.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted, heterocycle, hetaryl, substituted hetaryl, nitro, cyano, thiol, sulfamido and the like.

"Aralkyl" refers to the group —R—Ar where Ar is an aryl group and R is lower alkyl or substituted lower alkyl group. Aryl groups can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Heteroalkyl" refers to the group —R—Het where Het is a heterocycle group and R is a lower alkyl group. Heteroalkyl groups can optionally be unsubstituted or substituted with e.g., halogen, lower alkyl, lower alkoxy, alkylthio, acetylene, amino, amido, carboxyl, aryl, aryloxy, heterocycle, substituted heterocycle, hetaryl, substituted hetaryl, nitro, cyano, thiol, sulfamido and the like.

"Heteroarylalkyl" refers to the group —R—HetAr where HetAr is an heteroaryl group and R lower alkyl or substituted lower alkyl. Heteroarylalkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido and the like.

"Cycloheteroalkyl" refers to a cycloalkyl group wherein one or more of the ring carbon atoms is replaced with a heteroatom (e.g., N, O, S or P).

"Substituted cycloheteroalkyl" refers to a cycloheteroalkyl group as herein defined which contains one or more substituents, such as halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloalkyl" denotes the group —R-cycloalkyl where cycloalkyl is a cycloalkyl group and R is a lower alkyl or substituted lower alkyl. Cycloalkyl groups can optionally be unsubstituted or substituted with e.g. halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido and the like.

"Alkyl cycloheteroalkyl" denotes the group —R-cycloheteroalkyl where R is a lower alkyl or substituted lower alkyl. Cycloheteroalkyl groups can optionally be unsubstituted or substituted with e.g. halogen, lower alkyl, lower alkoxy, alkylthio, amino, amido, carboxyl, acetylene, hydroxyl, aryl, aryloxy, heterocycle, substituted heterocycle, hetaryl, substituted hetaryl, nitro, cyano, thiol, sulfamido and the like.

The compounds of this invention can be prepared as outlined in schemes 1–5. Compounds having the general formula II:

Scheme 1

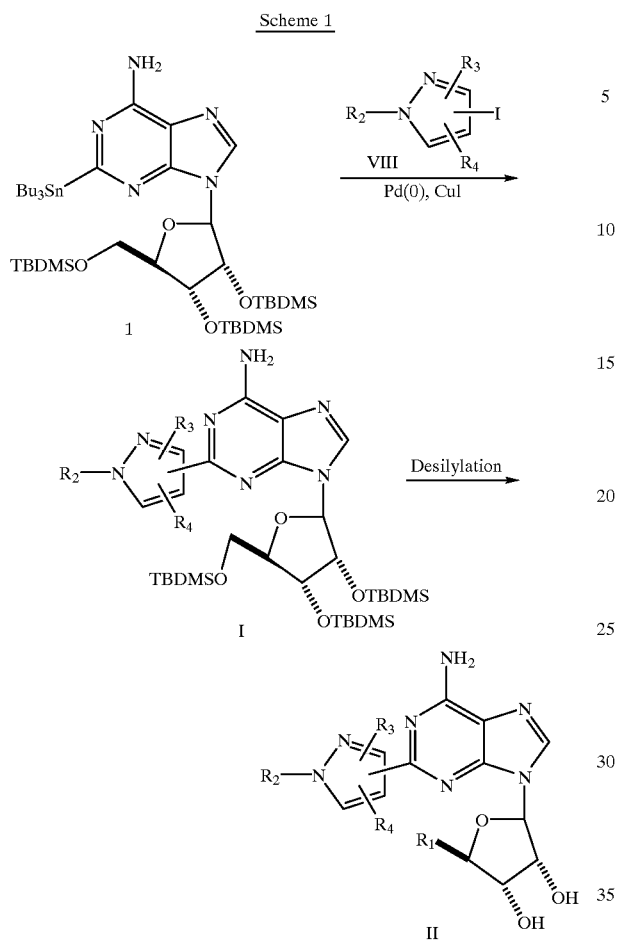

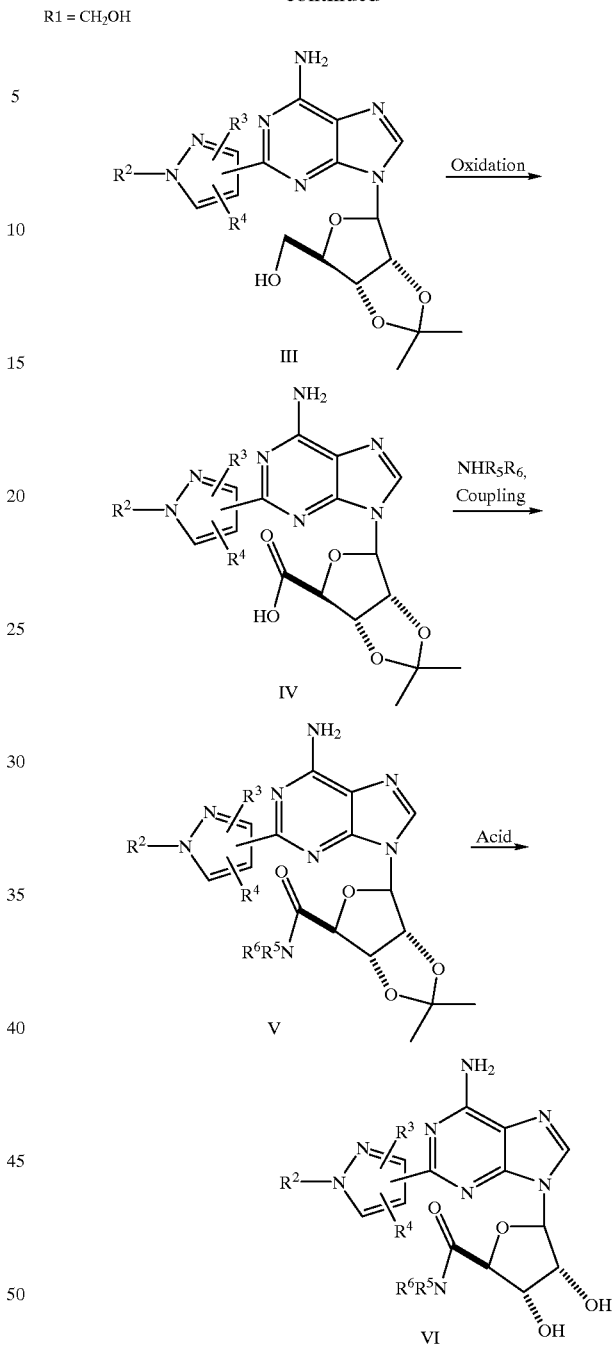

were prepared by the palladium mediated coupling of compound I with halo-pyrazoles represented by the formula VIII (scheme 4) in the presence or absence of copper salts (K. Kato et. al. J. Org. Chem. 1997, 62, 6833–6841; Palladium Reagents and Catalysts-Innovations in Organic Synthesis, Tsuji, John Wiley and Sons, 1995) followed by de-protection with either TBAF or NH4F (Markiewicz et. al Tetrahedron Lett.(1988), 29, 1561). The preparation of compound 1 has been previously described (K. Kato et. al. J. Org. Chem. 1997, 62, 6833–6841) and is outlined in scheme 5. Compounds with the general formula IV can ne prepared as shown in Scheme 2. Compound III which can be obtained by reacting II with 2,2-dimethoxypropane in presence of an

Scheme 2

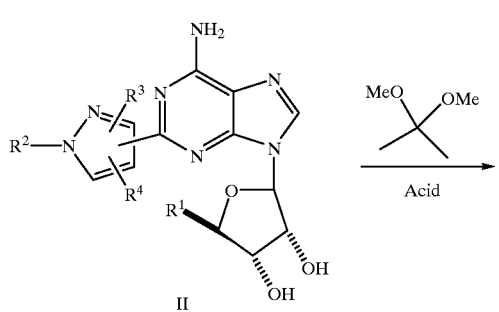

acid, can be oxidized to the carboxylic acid IV, based on structurally similar compounds, using potassium permanganate or pyridinium chlorochromate etc. ( Jones et.al., J. Am.Chem. Soc.(1949), 71, 3994.; Hudlicky, Oxidations in organic chemistry, American Chemical Society, Washington D. C., 1990) to compound IV. Reaction of primary or secondary amine of the formula NHR5R6, and compound IV using DCC (Fujino et.al., Chem. Pharm. Bull. (1974), 22, 1857), PyBOP (J. Martinez et. al., J. Med. Chem. (1988), 28, 1967) or PyBrop (J. Caste et.al. Tetrahedron, (1991), 32, 1967) coupling conditions can afford compound V. Deprotection of compound V can be performed by heating with 80% aq. acetic acid (T. W. Green and P. G. M. Wuts, (1991),Protective Groups in Organic Synthesis, A, Wiley-Interscience publication) or with anhydrous HCl (4N) to obtain compound of the general formula VI.

Scheme 3

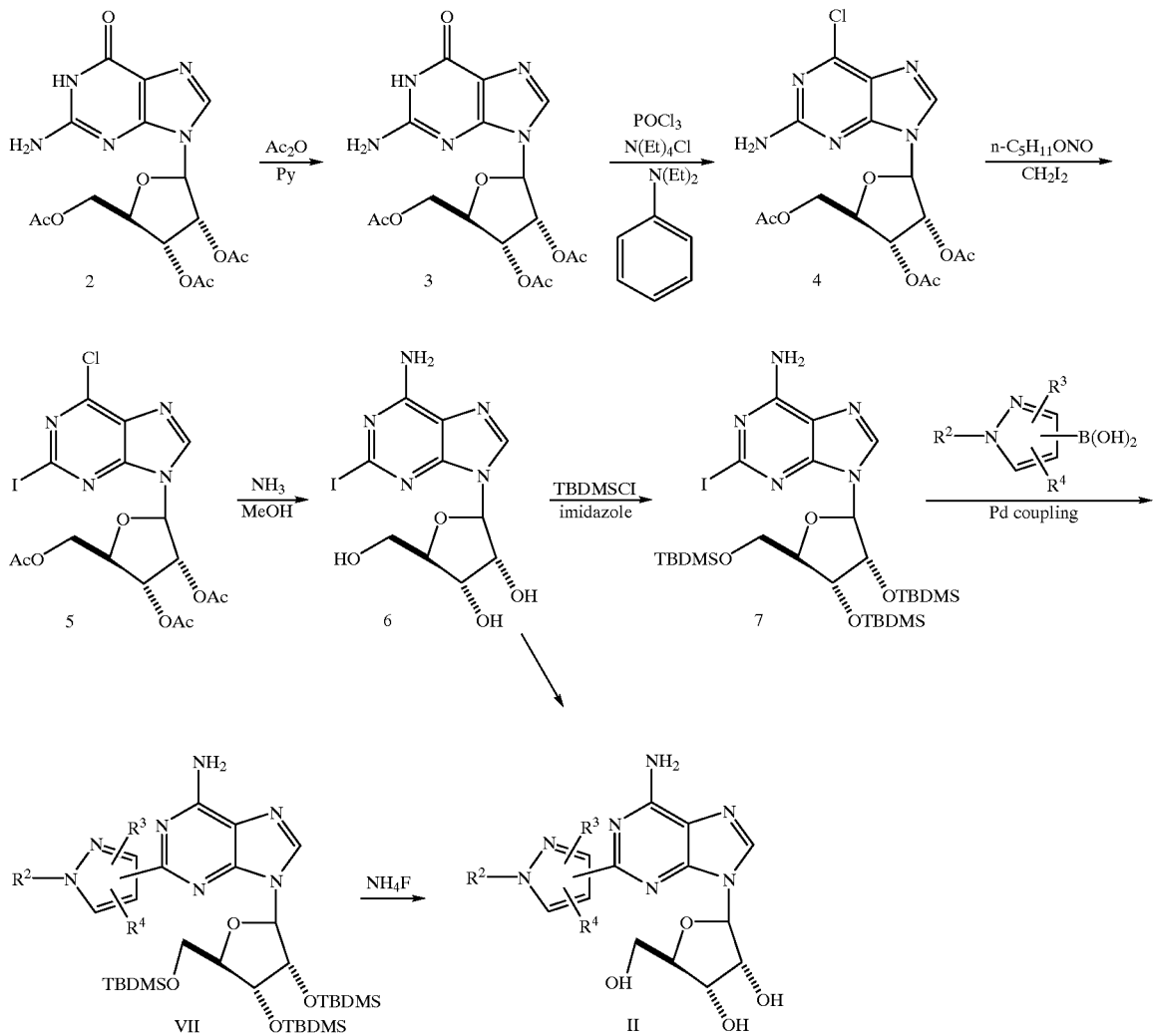

Alternatively, compounds with the general formula II can also be prepared by Suzuki type coupling as shown in the scheme 3. 2-Iodoadenosine 6 can be prepared in four steps from guanosine 2 following literature procedures (M. J. Robins et.al. Can. J. Chem. (1981), 59, 2601–2607; J. F. Cerstei et.al. Org. Synthesis, —242–243; V. Nair at. al., J. Org. Chem., (1988), 53, 3051–3057). Palladium mediated Suzuki coupling of 6 with appropriately substituted pyrazole-boronic acids XVII in presence of a base can provide final compounds with general formula II (A.Suzuli, Acc.Chem.Res) (1982), 15, 178). If necessary, 2',3',5' hydroxyls on 6 can be protected as TBDMS ethers prior to Suzuki coupling.

Compounds with the general formula VII can be either commercially available or prepared following the steps shown in scheme 4. Condensation of 1,3-diketo compounds of the formula IX with hydrazine in an appropriate solvent can give pyrazoles with the general formula X (R. H. Wiley et. al.Org.Synthsis, Coll. Vol IV (1963), 351. These pyrazoles can be N-alkylated with various alkyl halides to give compounds of the formula X which on iodination give 4-iodo derivatives with the general formula VIII (R. Huttel et.al. Justus Liebigs Ann.Chem.(1955), 593, 200).

5-iodopyrazoles with the general formula XV can be prepared following the steps outlined in the scheme 5. Condensation of 1,3-diketo compounds of the formula XII with hydrazine in an appropriate solvent can give pyrazoles with the general formula XIII. These pyrazoles can be N-alkylated with various alkyl halides to give compounds of the formula

Scheme 4

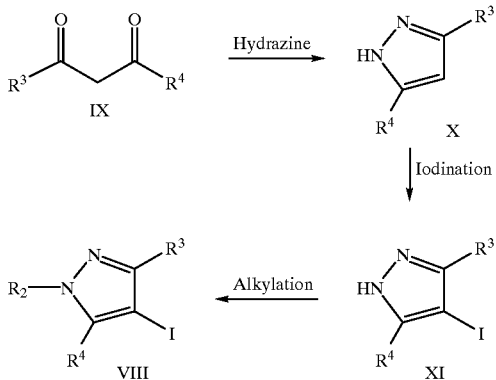

XIV. Abstraction of 5-H with a strong base followed by quenching with iodine can provide 5-iodo derivatives with general formula XV (F. Effenberger et. al. J. Org. Chem. (1984), 49, 4687).

Scheme 5

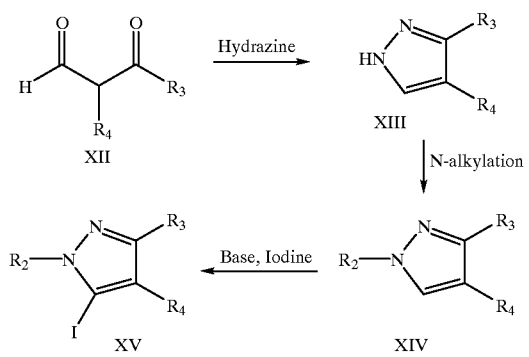

4- or 5- iodopyrazoles can be transformed into corresponding boronic acids as shown in the scheme 6. Transmetallation with n-buLi followed by treatment with trimethylborate can give compounds with the general formula XVI which on hydrolysis can provide boronic acids with the general formula XVII (F. C. Fischer et.al. RECUEIL (1965), 84, 439).

Scheme 6

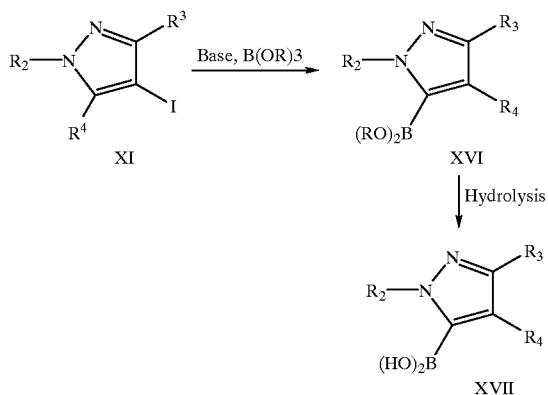

2-Stannyladenosine 1 was prepared in three steps from the commercially available 6-chloropurine riboside following

Scheme 7

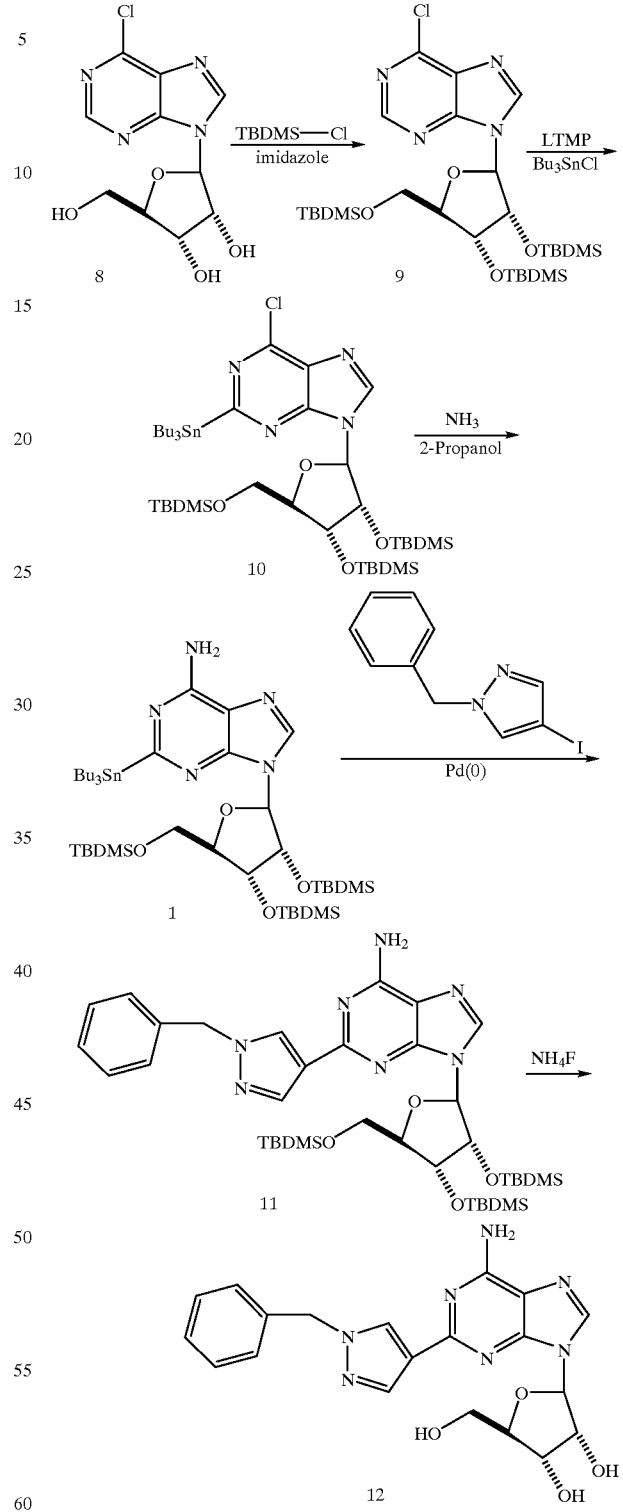

literature procedure (K. Kato et.al., J. Org. Chem. (1997), 62, 6833–6841). Tri TBDMS derivative was obtained by treating 8 with TBDMSCl and imidazole in DMF. Lithiation with LTMP followed by quenching with tri n-butyltin chloride gave exclusively 2-stannyl derivative 10. Ammonolysis in 2-propanol gave 2-stannyladenosine 1. Stille coupling of 1 with 1-benzyl-4-iodopyrazole in presence of Pd(PPh3)4 and CuI resulted in 11 (K. Kato et.al., J. Org. Chem. (1997), 62, 6833–6841). Deprotection of silyl groups on 2',3' and 5' hydroxyls with 0.5 M ammonium fluoride in methanol gave 12 in good yield (Scheme 7). Compounds 18–23 were prepared in similar manner. The methods used to prepare the compounds of this invention are not limited to those described above. Additional methods can be found in the following sources and are included by reference (J. March advanced Organic Chemistry; Reaction Mechanisms and Studies (1992), A Wiley Interscience Publications; and J. Tsuji, Palladium reagents and catalysts-Innovations in organic synthesis, John Wiley and Sons, 1995).

Compounds of this invention are useful in conjunction with radioactive imaging agents to image coronary activity. The compounds of this invention are $A_{2A}$ agonists that are believed to provide specific activation of adenosine $A_{2A}$ receptors in the coronary vessels as opposed to adenosine $A_1$ receptors in the atrium and AV-node and/or $A_{2B}$ receptors in peripheral vessels, thus avoiding undesirable side-effects. Upon administration in a therapeutic amount, the compositions of this invention cause coronary blood vessels to vasodilate to induce coronary steal wherein healthy coronary vessels steal blood from unhealthy vessels resulting in lack of blood flow to heart tissues. Coronary imaging then identified coronary regions with healthy and unhealthy blood flow. Lower doses of the $A_{2A}$ agonists may provide beneficial coronary vasodilatation (less severe) in the treatment of chronic CAD.

As $A_{2A}$ agonists, the compositions of this invention are also useful in adjunctive therapy with angioplasty to induce dilation, inhibit platelet aggregation, and as a general anti-inflammatory agent. $A_{2A}$ agonists, such as the compositions of this invention, can provide the therapeutic benefits described above by preventing neutrophil activation (Purinergic Approaches in Experimental Therapeutics K. A. Jacobson and M. F. Jarvis 1997 Wiley, New York). The compounds of this invention are also effective against a condition called no-reflow in which platelets and neutrophils aggregate and block a vessel. AS $A_{2A}$ agonists, the compositions of this invention are effective against no-reflow by preventing neutrophil and platelet activation (e.g., they are believed to prevent release of superoxide from neutrophils). As $A_{2A}$ agonists, the compositions of this invention are also useful as cardioprotective agents through their anti-inflammatory action on neutrophils. Thus in situations when the heart will go through an ischemic state such as a transplant, they will be useful.

This invention also includes pro-drugs of the above-identified $A_{2A}$ agonists. A pro-drug is a drug which has been chemically modified and may be biological inactive at its site of action, but which will be degraded or modified by one or more enzymatic or in vivo processes to the bioactive form. The pro-drugs of this invention should have a different pharmacokinetic profile to the parent enabling improved absorption across the mucosal epithelium, better salt formulation and/or solubility and improved systemic stability. The above-identified compounds may be preferably modified at one or more of the hydroxyl groups. The modifications may be (1) ester or carbamate derivatives which may be cleaved by esterases or lipases, for example; (2) peptides which may be recognized by specific or non-specific proteinase; or (3) derivatives that accumulate at a site of action through membrane selection or a pro-drug form or modified pro-drug form, or any combination of (1) to (3) above.

The compositions may be administered orally, intravenously, through the epidermis or by any other means known in the art for administering a therapeutic agents. The method of treatment comprises the administration of an effective quantity of the chosen compound, preferably dispersed in a pharmaceutical carrier. Dosage units of the active ingredient are generally selected from the range of 0.01 to 100 mg/kg, but will be readily determined by one skilled in the art depending upon the route of administration, age and condition of the patient. This dose is typically administered in a solution about 5 minutes to about an hour or more prior to coronary imaging. No unacceptable toxicological effects are expected when compounds of the invention are administered in therapeutic amounts.

If the final compound of this invention contains a basic group, an acid addition salt may be prepared. Acid addition salts of the compounds are prepared in a standard manner in a suitable solvent from the parent compound and an excess of the acid, such as hydrochloric, hydrobromic, sulfuric, phosphoric, acetic, maleic, succinic, or methanesulfonic. The hydrochloric salt form is especially useful. If the final compound contains an acidic group, cationic salts may be prepared. Typically the parent compound is treated with an excess of an alkaline reagent, such as hydroxide, carbonate or alkoxide, containing the appropriate cation. Cations such as $Na^+$, $K^+$, $Ca^{+2}$ and $NH_4^+$ are examples of cations present in pharmaceutically acceptable salts. Certain of the compounds form inner salts or zwitterions which may also be acceptable.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxycellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule. It is preferred that the compositions of this invention are administered as a solution either orally or intravenously.

The Examples which follow serve to illustrate this invention. The Examples are intended to in no way limit the scope of this invention, but are provided to show how to make and use the compounds of this invention. In the Examples, all temperatures are in degrees Centigrade.

EXAMPLE 1

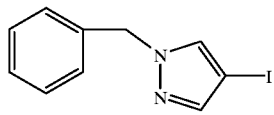

4-iodo-1-benzylpyrazole

To a solution of 4-iodopyrazole (400 mg, 2 mmol) in DMF(4 mL) at 0 C. was added sodiumhydride (80 mg, 60% dispersion in mineral oil, 2 mmol) followed by benzyl bromide (342 mg, 2 mmol) and reaction micture was allowed to stir for 2 h. Reaction mixture was concentrated in vacuo and the residue was purified by column chromatography to give N-benzylpyrazole in almost quantitative yield. IH NMR 5.29 (s, 2H), 7.18–7.28 (m,2H), 7.28–7.40 (m, 4H), 7.53 (s, 1H).

EXAMPLE 2

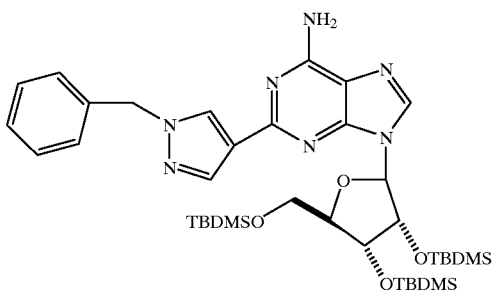

9-{(2R,3R,4R,5R-3,4-bis(1,1,2,2-tetramethyl-1silapropoxy)-5-[(1,1,2,2-tetramethyl-1-silapropoxy)methyl]oxolan-2-yl}-2-[1-benzylpyrazol-4-yl]purine-6-ylamine A mixture of compound 1 (50 mg, 0.056 mmol), N-benzyl-4-iodopyrazole 13 (50 mg, 0.183 mmol), Pd(PPh3)4 (20 mg(15 mol %) and CuI (40 mg, 0.2 mmol) in DMF (1 mL) was stirred at 90 C. for 16 h. The reaction was concentrated in vacuo and the residue was purified by preparative thin layer chromatography (methylene chloride:methanol 10:1) to afford compound 11: 1H NMR(CDCl3) 0.00(s, 3H, CH3), 0.01(s, 3H, CH3), 0.04(s, 3H, CH3), 0.07 (s, 3H, CH3), 0.11 (s, 3H, CH3),, 0.14 (s, 3H, CH3), 0.78 (s, 9H, t-bu), 0.83 (s, 9H, t-bu), 0.91 (s, 9H, t-bu), 3.80 (d, 1H), 4.05 (d, 1H), 4.11–4.12 (m, 1H), 4.33 (d, 1H), 4.50–4.52 (m, 1H), 5.35 (m, 2H), 5.65 (bs, 2H, D2O exchangeable), 6.05 (d, 1H), 7.28–7.40 (m, 5H), 7.98 (s, 1H), 8.18 (s, 1H), 8.22 (s, 1H).

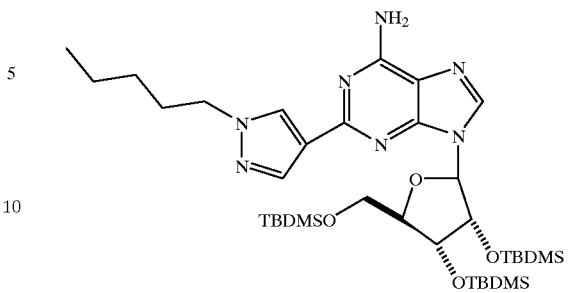

9-{(2R,3R,4R,5R)-3,4-bis(1,1,2,2-tetramethyl-1silapropoxy)-5-[(1,1,2,2-tetramethyl-1-silapropoxy)methyl]oxolan-2-yl}-2-[1-pentylpyrazol-4-yl]purine-6ylamine Compound was prepared in the manner of compound 11, substituting 4-iodo-pentpyrazole for 4-iodo-benzylpyrazole to afford compound 14: 1H NMR(CDCl3) 0.00(s, 3H, CH3), 0.01(s, 3H, CH3), 0.04(s, 3H, CH3), 0.07 (s, 3H, CH3), 0.11 (s, 3H, CH3),, 0.14 (s, 3H, CH3), 0.78 (s, 9H, t-bu), 0.80 (t, 3H), 0.83 (s, 9H, t-bu), 0.91 (s, 9H, t-bu), 1.25–1.40 (m, 4H), 1.85–1.95 (m, 2H), 3.82 (d, 1H), 4.08 (d, 1H), 4.20–4.28 (m, 3H), 4.32–4.34 (m, 1H), 4.55–4.57 (m, 1H), 5.35 (m, 2H), 5.70 (bs, 2H, D2O exchangeable), 6.08 (d, 1H), 7.28–7.40 (m, 5H), 8.05 (s, 1H), 8.15 (s, 1H), 8.20 (s, 1H).

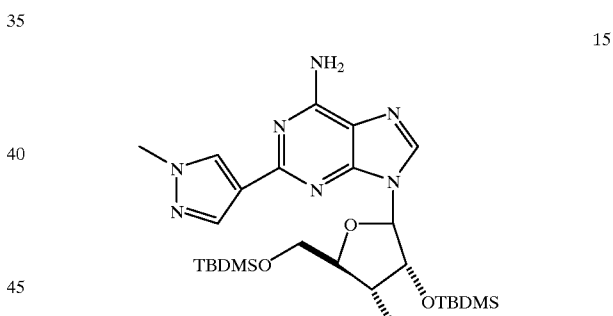

9-{(2R,3R,4R,5R)-3,4-bis(1,1,2,2-tetramethyl-1silapropoxy)-5-[(1,1,2,2-tetramethyl-1-silapropoxy)methyl]oxolan-2-yl}-2-[1-methylpyrazol-4-yl]purine-6-ylamine Compound was prepared in the manner of compound 11 substituting 4-iodo-methylpyrazole for 4-iodo-benzylpyrazole to afford compound 14: 1H NMR(CDCl3) 0.00 (s, 3H, CH3), 0.01 (s, 3H, CH3), 0.04 (s, 3H, CH3), 0.07 (s, 3H, CH3), 0.11 (s, 3H, CH3), 0.14 (s, 3 H, CH3), 0.78 (s, 9H, t-bu), 0.83 (s, 9H, t-bu), 0.91 (s, 9H, t-bu), 3.8 (d, 1H), 3.90 (s, 3H, N—CH3) 4.05 (d, 1H), 4.08–4.12 (m, 1H), 4.30–4.32 (m, 1H), 4.55–4.60 (m, 1H), 5.60 (bs, 1H, D2O exchangeable), 6.00–6.05 (m, 1H), 7.99 (s, 1H), 8.05 (s, 1H), 8.15 (s, 1H)

EXAMPLE 3

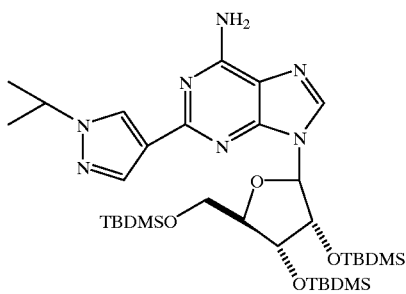

16

9{(2R,3R,4R,5R)-3,4-bis(1,1,2,2-tetramethyl-
1silapropoxy)-5-[1(1,1,2,2-tetramethyl-1-
silapropoxy)methyl]oxolan-2-yl}-2-[1-(1-
methylethyl)pyrazol-4-yl]purine-6ylamine Compound was prepared in the manner of compound 11 substituting 4-iodo-(1-methylethyl)pyrazole for 4-iodo-benzylpyrazole to afford compound 14: 1H NMR(CDCl3) 0.00 (s, 3H, CH3), 0.01 (s, 3H, CH3), 0.04 (s, 3H, CH3), 0.07 (s, 3H, CH3), 0.11 (s, 3H, CH3),, 0.14 (s, 3 H, CH3), 0.78 (s, 9H, t-bu), 0.83 (s, 9H, t-bu), 0.91 (s, 9H, t-bu), 1.55(d, 6H, C(CH3)2), 3.8 (d, 1H), 4.05 (d, 1H), 4.08–4.15 (m, 1H), 4.30–4.32 (m, 1H), 4.44–4.56 (m, 2H), 5.55(bs, 1H, D2O exchangeable), 6.05 (s, 1H), 8.05 (s, 1H), 8.10 (s, 1H), 8.2 (s, 1H)

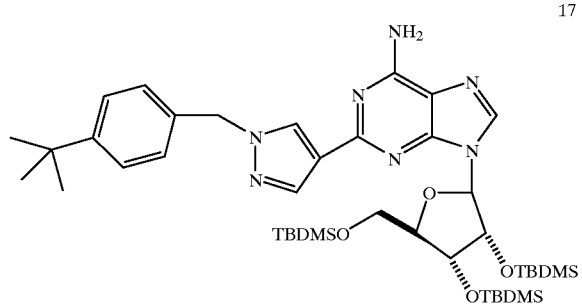

17

9-{(2R,3R,4R,5R)-3,4-bis(1,1,2,2-tetramethyl-
1silapropoxy)-5-[(1,1,2,2-tetramethyl-1-silapropoxy)
methyl]oxolan-2-yl}-2-[1-(4-t-butylbenzyl)pyrazol-
4-yl]purine-6-ylamine Compound was prepared in the manner of compound 11 substituting 4-iodo-(4-t-butylbenzyl)pyrazole for 4-iodo-benzylpyrazole to afford compound 14: 1H NMR(CDCl3) 0.00 (s, 3H, CH3), 0.01 (s, 3H, CH3), 0.04 (s, 3H, CH3), 0.07 (s, 3H, CH3), 0.11 (s, 3H, CH3),, 0.14 (s 3 H, CH3), 0.78 (s, 9H, t-bu), 0.83 (s, (9H, t-bu), 0.91 (s, 9H, t-bu), 1.30 (s, 9H, t-bu), 3.8 (d, 1H), 4.05 (d, 1H), 4.08–4.15(m, 1H), 4.30–4.32 (d, 1H), 4.47–4.49 (dd, 1H), 5.44 (bs, 1H, D2O exchangeable), 6.01 (d, J=3.6 Hz, 1H), 7.2 (d, J=2.0 Hz, 2H), 7.35 (d, J=2.0 Hz, 2H), 7.99 (s, 1H), 8.14 (s, 1H), 8.20 (s, 1H)

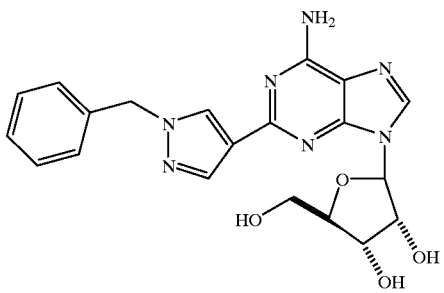

12

(4S,2R,3R,5R)-2-{6amino-2-[1-benzylpyrazol-4-yl]
purin-9-yl}-5-(hydroxymethyl)oxolane-3,4-diol A solution of triTBDMS derivative (25 mg, 0.035 mmol) in 0.5 M solution of NH4F in methanol (5 mL) was refluxed for 16 h. Reaction mixture was concentrated and residue was purified by preparative TLC (methanol-dichloromethane 9:1) to afford 12; 1H NMR (CD3OD) 3.65 (d, J=11.2 Hz, 1H), 3.81 (d, J=11.2 Hz, 1H), 4.18–4.19 (m, 1H), 4.26 (d, J=5.2 Hz, 1H), 4.78 (dd, 1H), 5.23 (s, 2H), 5.72 (d, J=7.2 Hz, 1H), 7.15–7.17 (m, 2H), 7.17–7.27 (m, 3H), 7.80 (s, 1H), 8.10 (s, 2H).

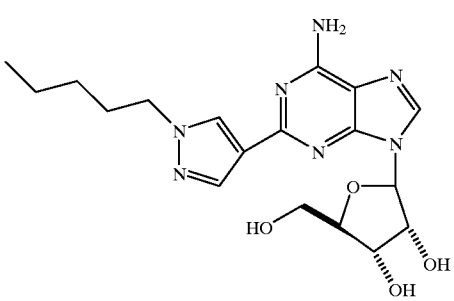

18

(4S,2R,5R)-2-[6-amino-2-(1-pentylpyrazol-4-yl)
purin 9-yl]-5-(hydroxymethyl)oxolane-3,4-diol Compound 18 was prepared in the manner of compound 12; 1H NMR (CD3OD) 4 0.8 (t, J=3.6 Hz, 3H), 1.20–1.26 (m, 4H), 1.76–1.80 (m, 2H), 3.67 (d, J=12.0 Hz, 1H), 3.85 (d, J=12.0 Hz, 1H), 4.03 (t, J=7.2 Hz, 2H), 4.19–4.20 (m, 1H), 4.28 (d, J=1.2 Hz, 1H), 4.78 (dd, 1H), 5.73 (d, J=7.2 Hz, 1H), 7.80 (s, 1H), 8.05 (s, 1H), 8.07 (s, 1H).

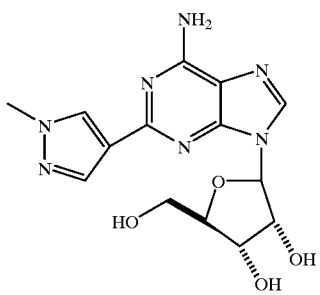

(4S,2R,3R,5R)-2-[6amino-2-1-methylpyrazol-4-yl)purin-9-yl]-5-(hydroxymethyl)oxolane-3,4diol Compound 19 was prepared in the manner of compound 12; 1H NMR (CD3OD) 3.60 (d, J=9.2 Hz, 1H), 3.78 (s, 3H, N—CH3), 3.80 (d, J=9.2 Hz, 1H), 4.10–4.12 (m, 1H), 4.24 (d, J=1.4 Hz, 1H), 4.78 (dd, 1H), 5.69 (d, J=7.0 Hz, 1H), 7.80 (s, 1H), 7.98 (s, 1H), 8.01 (s, 1H).

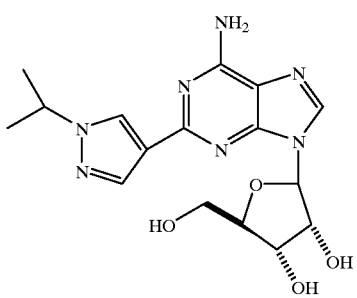

(4S,2R,3R,5R)-2-{6-amino-2-[1-(methylethyl)pyrazol-4-yl]purin-9-yl}-5-(hydroxymethyl)oxolane-3,4-diol Compound 20 was prepared in the manner of compound 12; 1H NMR (CD3OD) 1.41 (d, J=6.8 Hz, 6H), 3.66 (d, J=9.0 Hz, 1H), 3.80 (d, J=9.0 Hz, 1H), 4.16–4.18 (m, 1H), 4.25 (d, J=4.8 Hz, 1H), 4.40 (septet, 1H), 4.77 (dd, 1H), 5.71 (d, J=7.2 Hz, 1H), 7.80 (s, 1H), 8.03 (s, 1H), 8.13 (s, 1H).

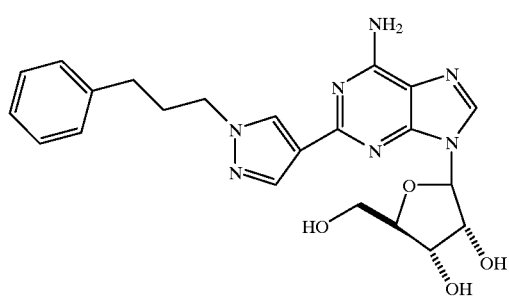

(4S,2R,3R5R)-2-{6-amino-2-[1-(3-phenylpropyl)pyrazol-4-yl]purin-9-yl}-5-(hydroxymethyl)oxolane-3,4-diol Compound 21 was prepared in the manner of compound 12; 1H NMR (CD3OD) 2.10 (t, J=6.7 Hz, 2H, CH2), 2.51 (t, J=6.7 Hz, 2H, CH2), 3.65 (d, J=9.2 Hz, 1H), 3.80 (d, J=9.2 Hz, 1H), 4.04 (t, J=6.7 Hz, 1H), 4.16–4.17 (m, 1H), 4.25 (d, J=1.2 Hz, 1H), 4.79 (dd, 1H), 5.71 (d, J=7.2 Hz, 1H), 7.05–7.07 (m, 2H), 7.16–7.24 (m, 3H), 7.80 (s, 1H), 8.06 (s, 1H), 8.08 (s, 1H).

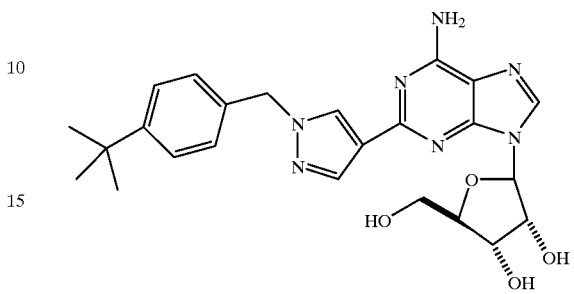

(4S,2R,3R,5R)-2-{6-amino-2-[1-(4-t-butylbenzyl)pyrazol-4-yl]purin-9-yl}-5-(hydroxymethyl)oxolane-3,4-diol Compound 22 was prepared in the manner of compound 12; 1H NMR (CD3OD) 1.15 (s, 9h, t-bu) 3.55 (d, J=11.2 Hz, 1H), 3.75 (d, J=11.2 Hz, 1H), 4.18–4.19 (m, 1H), 4.26 (d, J=5.2 Hz, 1H), 4.65 (dd, 1H), 5.12 (s, 2H), 5.65 (d, J=7.2 Hz, 1H), 7.05 (d, 2H), 7.17 (d, 3H), 7.75 (s, 1H), 8.05 (s, 2H).

(4S,2R,3R,5R)-2-(6-amino-2-pyrazol-4-ylpurin-9-yl)-5-hydroxymethyl)oxolane-3,4-diol Compound 23 was prepared in the manner of compound 12; 1H NMR (CD3OD) 3.75 (d, 1H, 5'—CH), 3.90 (d, 1 H,, 5'—CH), 4.15 (d, 2 H, 4'—CH) 4.35 (m, 1 H, 3'—CH), 4.85 (m, 1 H, 2'—CH), 5.95 (d, 1 H, 1'—CH), 8.20 (s, 1 H, 8-H), 8.25 (s, 2 H, Ar).

EXAMPLE 4

Compositions of this invention were assayed to determine their affinity for the A2A receptor in a pig striatum membrane prep. Briefly, 0.2 mg of pig striatal membranes were treated with adenosine deaminase and 50 mM Tris buffer (pH=7.4) followed by mixing. To the pig membranes was added 2 microL of serially diluted DMSO stock solution of the compounds of this invention at concentrations ranging from 100 microM to 10 nM or the control received 2 microL of DMSO alone, then the tritiated antagonist ZM 241385 in Tris buffer (50 mM, pH of 7.4) was added to achieve a final concentration of 2 nM. After incubation at 23 C. for 2h, then the solutions were filtered using a membrane harvester using multiple washing of the membranes (3×). The filter disks were counted in scintillation cocktail affording the amount of displacement of tritiated ZM by the competitive binding this invention. Greater than a 5 point curve was used to generate IC50's and the number of experiments is indicated in the column marked in Table 1 below.

TABLE 1

| Compound Number | $A_{2a}$ Ki (nM) | n |
|---|---|---|
| 12 | 6674 ± 1121 | 3 |
| 18 | 7089 ± 780 | 3 |
| 19 | >10,000 | 1 |
| 20 | −10,000 | 1 |
| 21 | 6133 ± 582 | 2 |
| 22 | 7680 | 1 |
| 23 | >100,000 | 1 |

What we claim is:

1. A composition of matter having the formula:

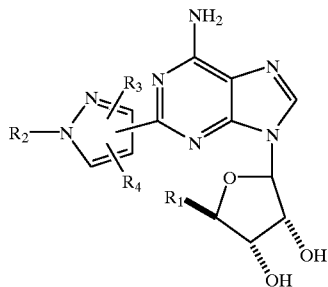

wherein $R^1$ is —$CH_2OH$, and —$C(=O)NR^5R^6$;

$R^2$ is selected from the group consisting of hydrogen, $C_{1-15}$ alkyl, $C_{2-15}$ alkenyl, $C_{2-15}$ alkynyl, heterocyclyl, aryl, and heteroaryl, wherein the alkyl, alkenyl, alkynyl, aryl, heterocyclyl, and heteroaryl substituents are optionally substituted with from 1 to 3 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2 NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ wherein the alkyl, alkenyl, alkynyl, aryl, heterocyclyl, and heteroaryl substituents are optionally substituted with from 1 to 3 substituents individually selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON (R^{20})_2$, $N(R^{20})_2 NR^{20}COR^{22}$, $NR^{20}CO_2R^{22}$, $NR^{20}CON (R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional heterocyclyl, aryl, and heterocyclyl substituent is optionally substituted with halo, $NO_2$, alkyl, $CF_3$, amino, mono- or di- alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

$R^3$, $R^4$ are each individually selected from the group consisting of hydrogen, $C_{1-15}$ alkyl, $C_{2-15}$ alkenyl, $C_{2-15}$ alkynyl, heterocyclyl, aryl, and heteroaryl, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2 NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ wherein the alkyl, alkenyl, alkynyl, aryl, heterocyclyl, and heteroaryl substituents are optionally substituted with from 1 to 3 substituents individually selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON (R^{20})_2$, $N(R^{20})_2 NR^{20}COR^{22}$, $NR^{20}CO_2R^{22}$, $NR^{20}CON (R^{20})_2$, $NR^{20}C(NR^{20})NHR^{23}$, $COR^{20}$, $CO_2R^{20}$, $CON (R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional heterocyclyl, aryl, and heterocyclyl substituent is optionally substituted with halo, $NO_2$, alkyl, $CF_3$, amino, mono- or di- alkylamino, alkyl or aryl or heteroaryl amide, $NCOR^{22}$, $NR^{20}SO_2R^{22}$, $COR^{20}$, $CO_2R^{20}$, $CON (R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

$R^5$ and $R^6$ are each individually H, $C_{1-15}$ alkyl with from 1 to 2 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2 NR^{20}COR^{22}$, $NR^{20}CO_2R^{22}$, $NR^{20}CON(R^{20})_2$, $NR^{20}C (NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional heteroaryl, aryl, and heterocyclyl substituent is optionally substituted with halo, $NO_2$, alkyl, $CF_3$, amino, mono- or di- alkylamino, alkyl or aryl or heteroaryl amide, $NCOR^{22}$, $NR^{20}SO_2R^{22}$, $COR^{20}$, $CO_2R^{20}$, $CON (R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, or $OR^{20}$;

$R^{20}$ is selected from the group consisting of H, $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl; and $R^{22}$ is a member selected from the group consisting of $C_{1-15}$ alkyl, $C_{2-15}$ alkenyl, $C_{2-15}$ alkynyl, heterocyclyl, aryl, and heteroaryl, wherein the alkyl, alkenyl, alkynyl, heterocyclyl, aryl, and heteroaryl substituents are optionally substituted with from 1 to 3 substituents independently selected from halo, alkyl, mono- or dialkylamino, alkyl or aryl or heteroaryl amide, CN, O—$C_{1-6}$ alkyl, $CF_3$, and heteroaryl wherein, when $R^1=CH_2OH, R^3$ is H, $R^4$ is H, and the pyrazole ring is attached through $C^4$, and $R^2$ is not H.

2. The composition of claim 1 wherein $R^2$ is selected from the group consisting of hydrogen, $C_{1-15}$ alkyl, $C_{2-15}$ alkynyl, heterocyclyl, aryl, and heteroaryl, wherein the alkyl, alkynyl, aryl, heterocyclyl, and heteroaryl substituents are optionally substituted with from 1 to 3 substituents independently selected from the group consisting of halo, $NO_2$, heterocyclyl, aryl heteroaryl, $CF_3$, CN, $OR^{20}$, $SR^{20}$ $N(R^{20})_2$, $S(O)R^{22}$, $SO_2R^{22}$, $SO_2N(R^{20})_2$, $COR^{20}$, $CO_2R^{20}$, $CON(R^{20})_2$, and wherein each optional heteroaryl, aryl, and heterocyclyl substituent is optionally substituted with halo, alkyl, $CF_3$ CN, and $OR^{20}$;

$R^3$ and $R^4$ are each individually selected from the group consisting of hydrogen, $C_{1-15}$ allyl, $C_{2-15}$ alkynyl, heterocyclyl, aryl, heteroaryl, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $COR^{20}$, $CO_2R^{20}$, $CON(R^{20})_2$, wherein the alkyl, alkynyl, aryl, heterocyclyl, and heteroaryl substituents are optionally substituted with from 1 to 3 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $COR^{20}$, $CO_2R^{20}$, $CON(R^{20})_2$, and wherein each optional heteroaryl, aryl, and heterocyclyl substituent is optionally substituted with halo, alkyl, $CF_3$ CN, and $OR^{20}$;

$R^5$ and $R^6$ are each individually selected from H, and $C_{1-15}$ alkyl having from 1 to 2 substituents independently selected from he group consisting of aryl, heteroaryl, $CF_3$, $OR^{20}$, and wherein each optional heteroaryl, and aryl substituent is further optionally substituted with halo, alkyl, and $CF_3$;

$R^{20}$ is a member selected from the group consisting of H, $C_{1-6}$ alkyl, aryl, and heteroaryl; and $R^{22}$ is a member selected from the group consisting of $C_{1-6}$ alkyl, aryl, and heteroaryl, wherein the alkyl, aryl, and heteroaryl substituents are optionally substituted with from 1 to 3 substituents independently selected from halo, alkyl, CN, O—$C_{1-6}$ alkyl, and $CF_3$.

3. The composition of claim 1 wherein $R^2$ is selected from the group consisting of hydrogen, $C_{1-15}$ alkyl, $C_{2-15}$ aryl, and heteroaryl, wherein the alkyl, aryl, and heteroaryl substituents are optionally substituted with from 1 to 3 substituents independently selected from the group consisting of halo, aryl, heteroaryl, $CF_3$, CN, $OR^{20}$, $SR^{20}$, $S(O)R^{22}$, $CO_2R^{20}$, $CON(R^{20})_2$, and wherein each optional heteroaryl, and aryl substituent is optionally substituted with halo, alkyl, $CF_3$ CN, and $OR^{20}$;

$R^3$ and $R^4$ are each individually selected from the group consisting of hydrogen, $C_{1-15}$ alkyl, $C_{2-15}$ aryl, heteroaryl, halo, $CF_3$, CN, $OR^{20}$, $SR^{20}$, $S(O)R^{22}$, $CO_2R^{20}$, and $CON(^{20})_2$, wherein the alkyl, aryl, and heteroaryl substituents are optionally substituted with from 1 to 3 substituents independently selected from the group consisting of halo, aryl, heteroaryl, $CF_3$, CN, $OR^{20}$, $SR^{20}$, $S(O)R^{22}$, $CO_2R^{20}$, and $CON(R^{20})_2$, and wherein each optional heteroaryl, and aryl substituent is optionally substituted with halo, alkyl, $CF_3$ CN, and $OR^{20}$;

$R^5$ and $R^6$ are each individually selected from H, and $C_{1-15}$ alkyl having from 1 to 2 substituents selected from $CF_3$;

$R^{20}$ is selected from H, and $C_{1-6}$; and $R^{22}$ is $C_{1-6}$ alkyl.

4. The composition of claim 1 wherein $R^2$ is independently selected from the group consisting of hydrogen, $C_{1-15}$ alkyl, and heteroaryl, wherein the alkyl, aryl and heteroaryl substituents are optionally substituted with from 1 to 2 substituents independently selected from the group consisting of halo, aryl, heteroaryl, $CF_3$, CN, $OR^{20}$, $CO_2R^{20}$, and $CON(R^{20})_2$, and wherein each optional heteroaryl, and aryl substituent is optionally substituted with halo, alkyl, $CF_3$ and CN;

$R^3$ and $R^4$ are each individually selected from the group consisting of hydrogen, $C_{1-15}$ alkyl, $C_{2-15}$ aryl, heteroaryl, halo, $CF_3$, CN, $OR^{20}$, $CO_2R^{20}$, and CON $(R^{20})_2$, wherein the alkyl, aryl, and heteroaryl substituents are optionally substituted with from 1 to 2 substituents independently selected from the group consisting of halo, aryl, heteroaryl, $CF_3$, CN, $OR^{20}$, $CO_2R^{20}$, and $CON(R^{20})_2$, and wherein each optional heteroaryl, and aryl substituent is optionally substituted with halo, alkyl, $CF_3$ or CN;

$R^5$ and $R^6$ are each individually selected from H, and $C_{1-15}$ alkyl;

$R^{20}$ is selected from H, and $C_{1-6}$; and $R^{22}$ is $C_{1-6}$ alkyl.

5. The composition of claim 1 wherein $R^2$ is independently selected from the group consisting of hydrogen, $C_{1-15}$ alkyl and aryl, wherein the alkyl and aryl substituents are optionally substituted with from 1 to 2 substituents independently selected from the group consisting of halo, $OR^{20}$, aryl, $CF_3$, CN, and wherein each optional aryl substituent is optionally substituted with halo, alkyl, $CF_3$ or CN;

$R^3$ and $R^4$ are each individually selected from the group consisting of hydrogen, $C_{1-15}$ alkyl, aryl, halo, $CF_3$, and CN, wherein the alkyl, and aryl substituents are optionally substituted with from 1 to 2 substituents independently selected from the group consisting of halo, aryl, $CF_3$, CN, and wherein each optional aryl substituent is optionally substituted with halo, alkyl, $CF_3$ or CN;

$R^5$ and $R^6$ are each individually selected from H, and $C_{1-15}$ alkyl; and $R^{20}$ is selected from H and $C_{1-6}$.

6. The composition of claims 1 or 2 or 3 or 4 or 5 wherein the point of attachment of the pyrazole zing is C-4.

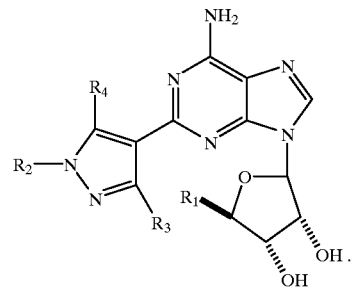

7. The composition of claims 1 or 2 or 3 or 4 or 5 wherein the point of attachment of the pyrazole ring is C-3.

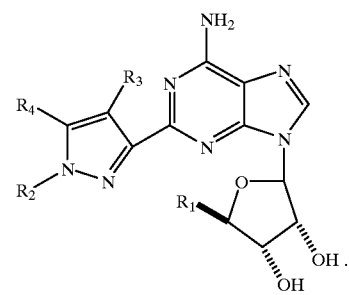

8. The composition of claims 1 or 2 or 3 or 4 or 5 wherein the point of attachment of the pyrazole ring is C-5.

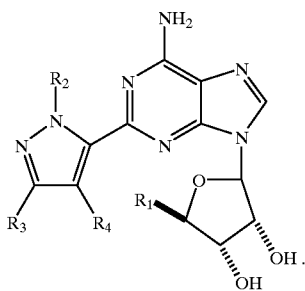

9. The composition of claims 6 or 7 or 8 wherein $R^1$=CH$_2$OH.

10. The composition of claim 6 wherein $R^1$ is —CH$_2$OH;
$R^2$ is independently selected from the group consisting of hydrogen, $C_{1-10}$ alkyl and aryl, wherein the alkyl and aryl substitutients are optionally substituted with from 1 to 2 substituents independently selected from the group consisting of halo, $OR^{20}$, aryl, CF$_3$, and CN, and wherein each optional aryl substituent is optionally substituted with halo, alkyl, CF$_3$ and CN;
$R^3$ and $R^4$ are each individually- selected from the group consisting of hydrogen, $C_{1-15}$ alkyl, aryl, halo, CF$_3$, and CN, wherein the alkyl, and aryl substituents are optionally substituted with a substituent independently selected from the group consisting of halo, CF$_3$, and CN; and
$R^{20}$ is selected from H, and $C_{1-6}$.

11. The composition of claim 6 wherein $R^1$ is —CH$_2$OH;
$R^2$ is independently selected from the group consisting of hydrogen, $C_{1-8}$ alkyl and aryl, wherein the alkyl and aryl substituents are optionally substituted with from 1 to 2 substituents independently selected from the group consisting of halo, $OR^{20}$, aryl, CF$_3$, and CN, and wherein each optional aryl substituent is optionally substituted with halo, alkyl, CF$_3$ and CN;
$R^3$ and $R^4$ are each individually selected from the group consisting of hydrogen, $C_{1-3}$ alkyl, aryl, halo, CF$_3$, CN; and
$R^{20}$ is selected from H, and $C_{1-6}$.

12. The composition of claim 6 wherein $R^1$ is —CH$_2$OH;
$R^2$ is independently selected from the group consisting of hydrogen, $C_{1-8}$ alkyl and aryl, wherein the alkyl and aryl substituents are optionally substituted with from 1 to 2 substituents independently selected from the group consisting of halo, $OR^{20}$, aryl, CF$_3$, and CN, and wherein each optional aryl substituent is optionally substituted with halo, alkyl, CF$_3$ and CN;
$R^3$ and $R^4$ are each individually selected from the group consisting of hydrogen, methyl, and halo; and
$R^{20}$ is selected from H, and $C_{1-6}$.

13. The composition of claim 6 wherein $R^1$ is —CH$_2$OH;
$R^2$ is independently selected from the group consisting of hydrogen, $C_{1-8}$ alkyl and aryl, wherein the alkyl and aryl substituents are optionally substituted with 1 substituent selected from the group consisting of halo, aryl, CF$_3$, and CN, and wherein each optional aryl substituent is optionally substituted with halo, alkyl, CF$_3$ and CN; and
$R^3$ and $R^4$ are each individually selected from the group consisting of hydrogen, and methyl.

14. The composition of claim 6 wherein $R^1$ is —CH$_2$OH;
$R^2$ is selected from the group consisting of hydrogen, and $C_{1-8}$ alkyl that is optionally substituted with 1 substituent selected from the group consisting of aryl, CF$_3$, and CN, and wherein each optional aryl substituent is optionally substituted with halo, alkyl, CF$_3$ and CN; and
$R^3$ and $R^4$ are each individually selected from the group consisting of hydrogen, and methyl.

15. The composition of claim 6 wherein $R^1$ is —CH$_2$OH;
$R^2$ is selected from the group consisting of hydrogen, and $C_{1-8}$ alkyl that is optionally substituted with one aryl substituent that is optionally substituted with halo, alkyl, CF$_3$ and CN; and
$R^3$ and $R^4$ are each hydrogen.

16. The composition of claim 6 wherein $R^1$ is —CH$_2$OH;
$R^2$ is selected from the group consisting of hydrogen, and $C_{1-6}$ allyl that is optionally substituted with aryl that is optionally substituted with alkyl; and
$R^3$ and $R^4$ are each hydrogen.

17. The composition of claim 7 wherein $R^1$ is —CH$_2$OH,
$R^2$ is selected from the group consisting of hydrogen, and $C_{1-8}$ alkyl that is optionally substituted with 1 substituent selected from the group consisting of aryl, CF$_3$, and CN, and wherein each optional aryl substituent is optionally substituted with halo, alkyl, CF$_3$ and CN; and
$R^3$ and $R^4$ are each individually selected from hydrogen, and methyl.

18. The composition of claim 7 wherein $R^1$ is —CH$_2$OH;
$R^2$ is selected from the group consisting of hydrogen, and $C_{1-8}$ alkyl that is optionally substituted with 1 substituent selected from the group consisting of aryl, and wherein each optional aryl substituent is optionally substituted with halo, alkyl, CF$_3$ and CN; and
$R^3$ and $R^4$ are each hydrogen.

19. The composition of claim 7 wherein $R^1$ is —CH$_2$OH;
$R^2$ is selected from the group consisting of hydrogen, and $C_{1-6}$ alkyl that is optionally substituted with aryl that is optionally substituted with alkyl; and
$R^3$ and $R^4$ are each hydrogen.

20. The composition of claim 8 wherein $R^1$ is —CH$_2$OH;
$R^2$ is selected from the group consisting of hydrogen, and $C_{1-6}$ alkyl;
$R^3$ is selected from the group consisting of hydrogen, $C_{1-6}$ alkyl, and aryl, wherein the alkyl, and aryl substituents are optionally substituted with from 1 to 2 substituents independently selected from the group consisting of halo, aryl, CF$_3$, and CN, and wherein each optional aryl substituent is optionally substituted with halo, alkyl, CF$_3$ and CN; and
$R^4$ is selected from the group consisting of hydrogen and $C_{1-6}$ alkyl.

21. The composition of claim 8 wherein $R^1$ is —CH$_2$OH;
$R^2$ is selected from the group consisting of hydrogen, and methyl;
$R^3$ and $R^4$ are each independently selected from the group consisting of hydrogen, and $C_{1-6}$ alkyl, that is optionally substituted with aryl that is optionally substituted with alkyl; and
$R^4$ is selected from hydrogen and methyl.

22. The composition of claim 6 wherein $R^1$ is —CONHEt;
$R^2$ is selected from the group consisting of hydrogen, and $C_{1-8}$ alkyl that is optionally substituted with 1 substituent selected from the group consisting of aryl, CF$_3$, and CN, and wherein each optional aryl substituent is optionally substituted with halo, alkyl, CF$_3$ and CN; and
$R^3$ and $R^4$ are each individually selected from the group consisting of hydrogen, and methyl.

23. The composition of claim 6 wherein $R^1$ is —CONHEt;

$R^2$ is selected from the group consisting of hydrogen, and $C_{1-8}$ alkyl that is optionally substituted with 1 aryl substituent of aryl, that is optionally substituted with halo, alkyl, $CF_3$ and CN; and $R^3$ and $R^4$ are each hydrogen.

24. The composition of claim 6 wherein $R^1$ is —CONHEt;

$R^2$ is selected from the group consisting of hydrogen, and $C_{1-6}$ alkyl that is optionally substituted with aryl that is optionally substituted with alkyl; and $R^3$ and $R^4$ are hydrogen.

25. The composition of claim 7 wherein $R^1$ is —CONHEt;

$R^2$ is selected from the group consisting of hydrogen, and $C_{1-8}$ that is optionally substituted with 1 aryl substituent that is optionally substituted with halo, alkyl, $CF_3$ and CN; and $R^3$ and $R^4$ are hydrogen.

26. The composition of claim 7 wherein $R^1$ is —CONHEt;

$R^2$ is independently selected from the group consisting of hydrogen, and $C_{1-6}$ alkyl that is optionally substituted with amyl that is optionally substituted with alkyl; and $R^3$ and $R^4$ are each hydrogen.

27. The composition of claim 8 wherein $R^1$ is —CONHEt; and $R^2$ is selected from hydrogen, and methyl;

$R^3$ and $R^4$ are each individually selected from the group consisting of hydrogen, and $C_{1-6}$ alkyl, wherein the alkyl, is optionally substituted with aryl that is optionally substituted with alkyl; and $R^4$ is selected from hydrogen and methyl.

28. The composition of claim 1 wherein the compound is selected from (4S,2R,3R,5R)-2-{6-amino-2-[1-benzylpyrazol-4-yl]-purin-9-yl}-5-(hydroxymethyl) oxolane-3,4-diol, (4S,2R,3R,5R)-2-[6-amino-2-(1-pentylpyrazol-4-yl)purin-9-yl]-5-(hydroxymethyl)oxolane-3,4-diol, (4S,2R,3R,5R)-2-[6-amino-2-(1-methylpyrazol-4-yl)purin-9-yl]-5-(hydroxymethyl)oxolane-3,4-diol, (4S,2R,3R,5R)-2-{6-amino-2-[1-(methylethyl)pyrazol-4yl]purin-9-yl}-5-(hydroxymethyl)oxolane-3,4-diol, (4S,2R,3R,5R)-2-{6-amino-2-[1-(3-phenylpropyl)pyrazol-4-yl]purin-9-yl}-5-(hydroxymethyl)oxolane-3,4-diol, (4S,2R,3R,5R)-2-{6-amino-2-[1-(4-t-butylbenzyl)pyrazol-4-yl]purin-9-yl}-5-(hydroxymethyl)oxolane-3,4-diol, (4S,2R,3R,5R)-2-(6-amino-2-pyrazol-4ylpurin-9-yl)-5-(hydroxymethyl) oxolane-3,4-diol, and mixtures thereof.

29. A method for stimulating coronary vasodilatation in a mammal by administering to the mammal a therapeutically effective amount of a compound of claim 1 that is sufficient to stress the heart and induce a coronary steal situation for the purposes of imaging the heart.

30. The method of claim 29 wherein the therapeutically effective amount ranges from about 0.01 to about 100 mg/kg weight of the mammal.

31. The method of claim 29 wherein the mammal is a human.

32. A pharmaceutical composition of matter comprising the composition of claim 1 and one or more pharmaceutical excipients.

33. The pharmaceutical composition of matter of claim 32 wherein the pharmaceutical composition is in the form of a solution.

\* \* \* \* \*

UNITED STATES PATENT AND TRADEMARK OFFICE
CERTIFICATE OF CORRECTION

PATENT NO. : 6,214,807 B1
DATED : April 10, 2001
INVENTOR(S) : Zablocki et al.

It is certified that error appears in the above-identified patent and that said Letters Patent is hereby corrected as shown below:

Title page,
Item [54], delete "C-Pyrazole $_{2A\,A}$ Receptor Agonists" and replace with -- C-Pyrazole $A_{2A}$ Receptor Agonists --

Column 1,
Line 1, delete "C-Pyrazole $_{2A\,A}$ Receptor Agonists" and replace with -- C-Pyrazole $A_{2A}$ Receptor Agonists --
Line 47, delete "$A_2A$" and replace with -- $A_{2A}$ --.

Column 5,
Line 49, delete "24" and replace with -- 2-4, --.

Column 7,
Line 25, delete "14" and replace with -- 1-4 --.

Column 11,
Line 52, delete "Cerstei" and replace with -- Cerstei --.
Line 60, delete "VII" and replace with -- VIII --.

Column 18,
Line 21, delete "6ylamine" and replace with -- 6-ylamine --.

Column 19,
Line 21, delete "6ylamine" and replace with -- 6-ylamine --.

Column 20,
Line 21, delete "6amino" and replace with -- 6-amino --.

Column 21,
Line 16, delete "6amino" and replace with -- 6-amino --.

Column 23,
Line 2, after the word binding insert the words -- compositions of --.
Line 54, delete "or" and replace with -- and --.

UNITED STATES PATENT AND TRADEMARK OFFICE
CERTIFICATE OF CORRECTION

PATENT NO. : 6,214,807 B1
DATED : April 10, 2001
INVENTOR(S) : Zablocki et al.

It is certified that error appears in the above-identified patent and that said Letters Patent is hereby corrected as shown below:

Column 24,
Line 16, delete "or" and replace with -- and --.

Column 25,
Line 54, after the word alkyl, and before the word and insert -- $C_{2-15}$ aryl, --.

Signed and Sealed this

Sixteenth Day of October, 2001

Attest:

*Nicholas P. Godici*

NICHOLAS P. GODICI
*Attesting Officer*      *Acting Director of the United States Patent and Trademark Office*

UNITED STATES PATENT AND TRADEMARK OFFICE
CERTIFICATE OF CORRECTION

PATENT NO. : 6,214,807 B1
DATED : April 20, 2001
INVENTOR(S) : Zablocki et al.

It is certified that error appears in the above-identified patent and that said Letters Patent is hereby corrected as shown below:

Column 20,
Line 57, delete "purin 9-yl]" and replace with -- purin-9-yl] --

Signed and Sealed this

Tenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,214,807 B1
DATED : April 10, 2001
INVENTOR(S) : Zablocki et al.

It is certified that error appears in the above-identified patent and that said Letters Patent is hereby corrected as shown below:

Column 20,
Line 56, delete "(4S,2R,5R)" and replace with -- (4S,2R,3R,5R) --

Signed and Sealed this

Eighteenth Day of January, 2005

JON W. DUDAS
*Director of the United States Patent and Trademark Office*